United States Patent
Komatsu

(10) Patent No.: US 10,993,649 B2
(45) Date of Patent: May 4, 2021

(54) BIOMETRIC INFORMATION PRESENTATION SYSTEM AND TRAINING METHOD

(71) Applicant: TOYOBO CO., LTD., Osaka (JP)

(72) Inventor: Yoko Komatsu, Otsu (JP)

(73) Assignee: TOYOBO CO., LTD., Osaka (JP)

( * ) Notice: Subject to any disclaimer, the term of this patent is extended or adjusted under 35 U.S.C. 154(b) by 0 days.

(21) Appl. No.: 16/650,512

(22) PCT Filed: Oct. 1, 2018

(86) PCT No.: PCT/JP2018/036678
§ 371 (c)(1),
(2) Date: Mar. 25, 2020

(87) PCT Pub. No.: WO2019/077984
PCT Pub. Date: Apr. 25, 2018

(65) Prior Publication Data
US 2020/0315485 A1 Oct. 8, 2020

(30) Foreign Application Priority Data
Oct. 19, 2017 (JP) .............................. JP2017-202746

(51) Int. Cl.
*A61B 5/024* (2006.01)
*A61B 5/352* (2021.01)
(Continued)

(52) U.S. Cl.
CPC .............. *A61B 5/352* (2021.01); *A61B 5/024* (2013.01); *A61B 5/02405* (2013.01); *A61B 5/25* (2021.01);
(Continued)

(58) Field of Classification Search
CPC ... A61B 5/0456; A61B 5/024; A61B 5/02405; A61B 5/0408; A61B 5/044;
(Continued)

(56) References Cited

U.S. PATENT DOCUMENTS

2006/0074333 A1* 4/2006 Huiku .................. A61B 5/0452
600/529
2011/0313303 A1* 12/2011 Higa .................... A61B 5/0245
600/500
(Continued)

FOREIGN PATENT DOCUMENTS

| CN | 101584580 | 11/2009 |
| JP | 8-71050 | 3/1996 |

(Continued)

OTHER PUBLICATIONS

International Search Report dated Oct. 23, 2018 in International (PCT) Application No. PCT/JP2018/036678.
(Continued)

*Primary Examiner* — Eugene T Wu

(57) ABSTRACT

A biometric information presentation system that enables efficient training by obtaining biometric information without giving a subject a sense of discomfort. The biometric information presentation system uses a garment-type biometric information measuring apparatus including at least fabric having a 20% elongation stress of 20 N or less. A garment pressure of the garment-type biometric information measuring apparatus is 0.1 kPa or more and 1.5 kPa or less. A skin contact-type electrode is provided at a portion of the garment-type biometric information measuring apparatus at which a garment pressure is 0.3 kPa or more. The garment-type biometric information measuring apparatus is worn by the subject. From obtained electrocardiographic information is calculated an RRI, an indicator of parasympathetic activity and indicator of sympathetic activity. The biometric
(Continued)

information presentation system presents this calculated result on a terminal device and presents an action based upon the result to achieve the efficient training.

15 Claims, 2 Drawing Sheets

(51) Int. Cl.
  *A61B 5/00* (2006.01)
  *A61B 5/25* (2021.01)
  *A61B 5/339* (2021.01)
(52) U.S. Cl.
  CPC ............ *A61B 5/339* (2021.01); *A61B 5/6804* (2013.01); *A61B 5/6879* (2013.01); *A61B 2503/10* (2013.01)
(58) Field of Classification Search
  CPC . A61B 5/6804; A61B 5/6879; A61B 2503/10; A61B 5/00; A61B 5/0478; A61B 5/16; A61B 69/00; A61B 5/486; A61B 5/18
  See application file for complete search history.

(56) References Cited

U.S. PATENT DOCUMENTS

2016/0045125 A1* 2/2016 Krueger ................ A61B 5/046
                                                    600/518
2016/0374615 A1* 12/2016 Tsukada ............. A61B 5/04085
                                                    600/382
2019/0261921 A1*  8/2019 Otsuka ................ A61B 5/0408

FOREIGN PATENT DOCUMENTS

| | | |
|---|---|---|
| JP | 08-290725 | 11/1996 |
| JP | 10-262942 | 10/1998 |
| JP | 2004-181218 | 7/2004 |
| JP | 2004-267296 | 9/2004 |
| JP | 2010-172365 | 8/2010 |
| JP | 4844523 | 12/2011 |
| JP | 2014-61079 | 4/2014 |
| JP | 2016-54814 | 4/2016 |
| WO | 2010/103817 | 9/2010 |

OTHER PUBLICATIONS

Written Opinion of the International Searching Authority dated Oct. 23, 2018 in International (PCT) Application No. PCT/JP2018/036678.
Korean Office Action dated Oct. 29, 2020 in corresponding Korean Application No. 10-2020-7013527 with Machine English Translation.
Chinese Office Action dated Dec. 25, 2020 in corresponding Chinese Application No. 201880067197.7, with Machine English Translation.

* cited by examiner

[FIG. 1]
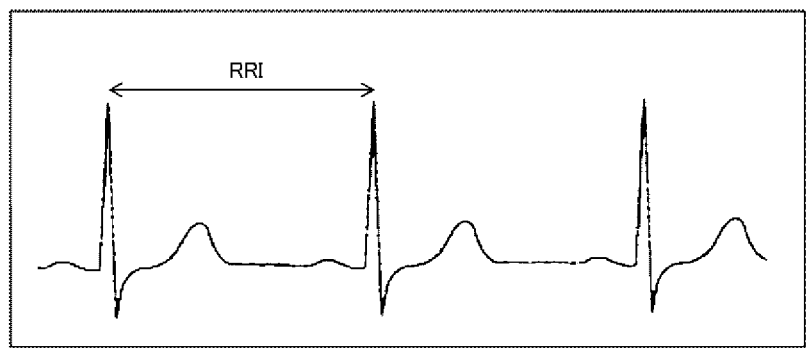
[FIG. 2]
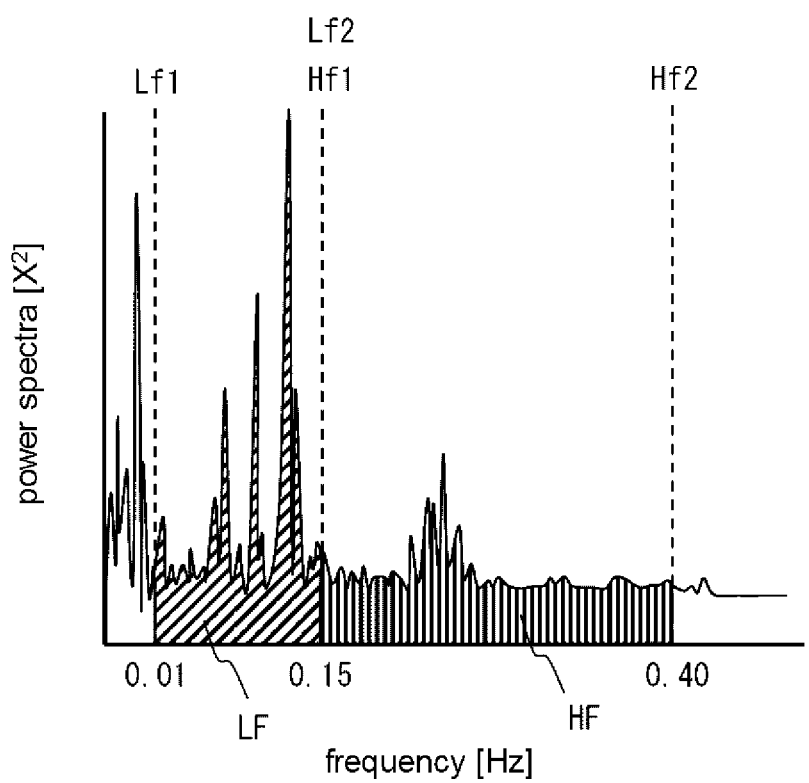
[FIG. 3]
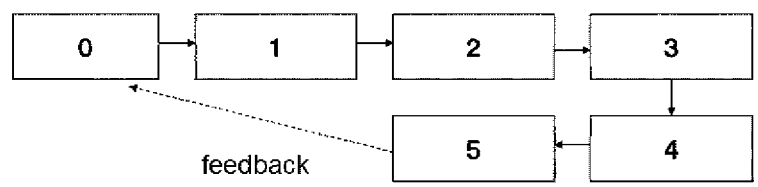

[FIG. 4]
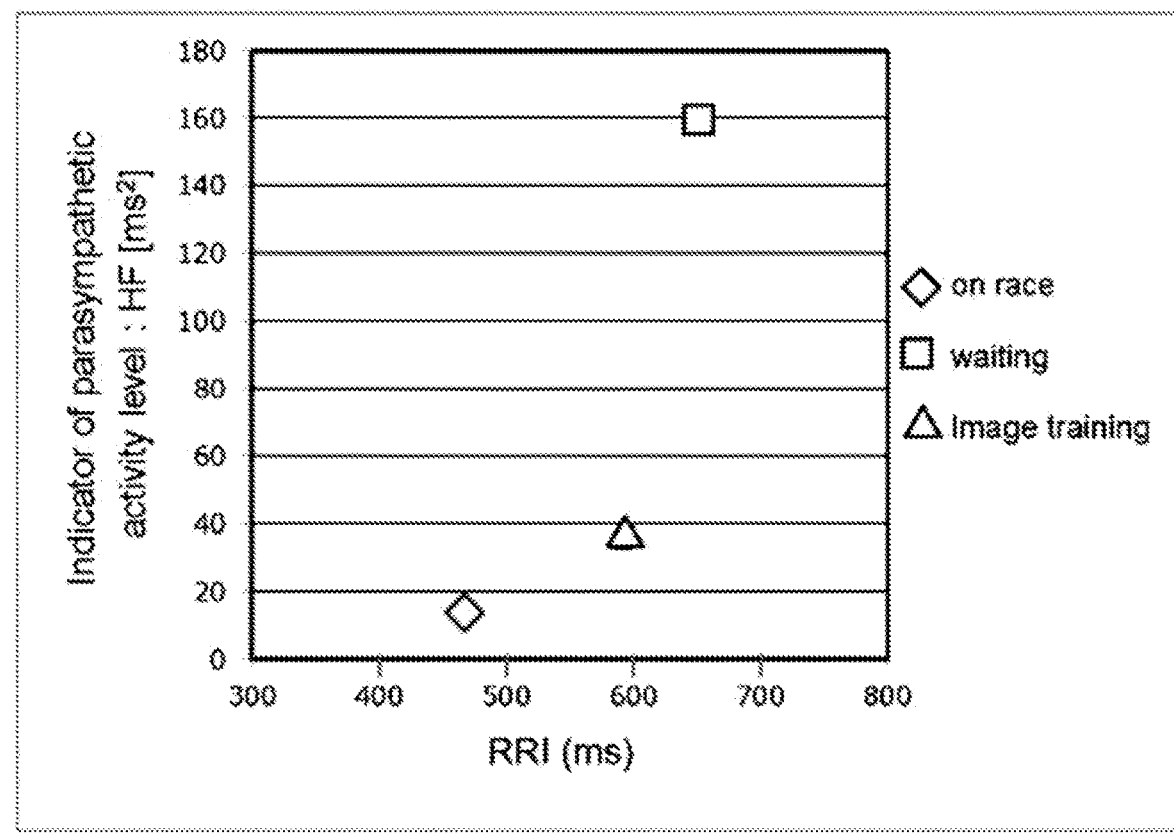
[FIG. 5]
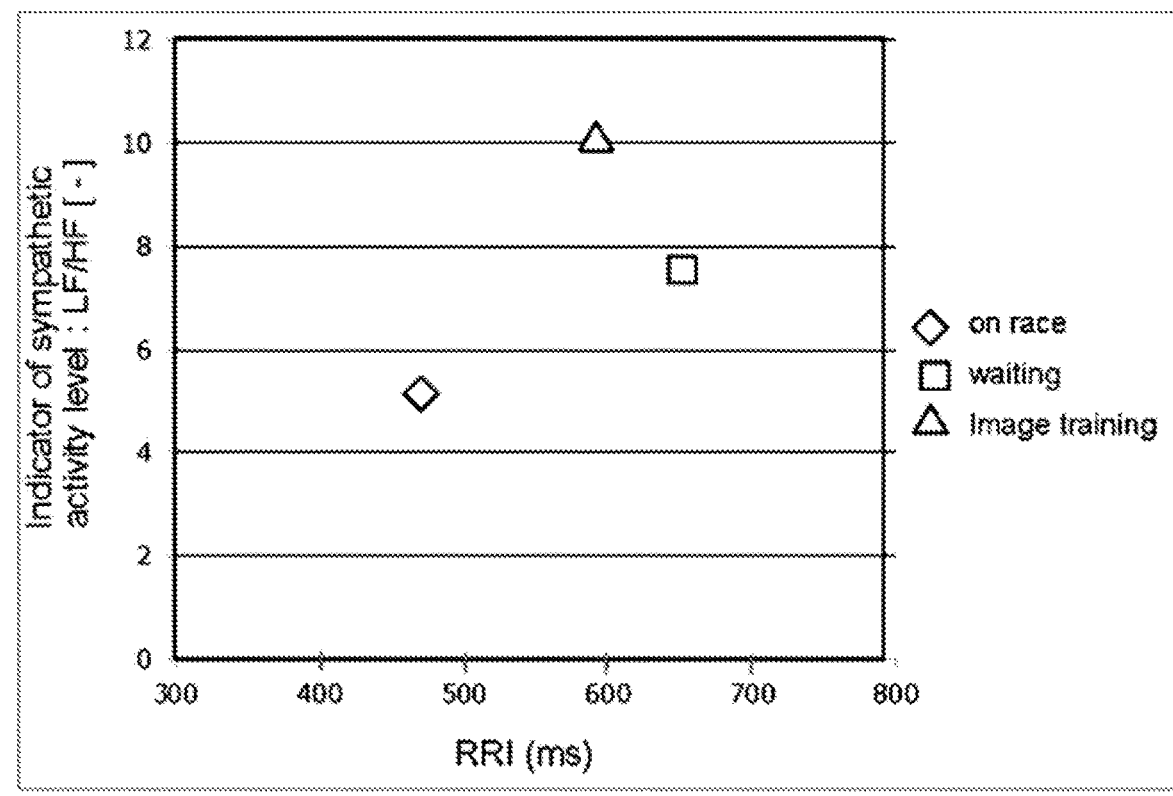

BIOMETRIC INFORMATION PRESENTATION SYSTEM AND TRAINING METHOD

TECHNICAL FIELD

The present invention relates to a system that converts biometric information obtained with a garment-type biometric information measuring apparatus, which is a wearable sensing device, to information indicating a mental state and/or a physiological state of a wearer, and that presents the information to the wearer or a third party in real time. More specifically, the present invention relates to a training method for performing training of a machine operation, sport or an instrumental performance with the system.

BACKGROUND ART

In training for an athlete, a martial artist, and the like, in various work training, and in self-development, an attempt to grasp a mental state and utilize it for training has been made.

Patent Document 1 discloses that satisfaction of a worker who is working on a machine is measured with brain waves and that a state of the satisfaction is fed back to the worker and further to the machine. This method is to evaluate satisfaction from physiological data, such as brain waves. However, a sense, such as the satisfaction, is a complex sense, and thus a specific mental state cannot be evaluated. For example, it is impossible to grasp a specific mental state such as whether the satisfaction has been generated by relaxation, sleepiness or awakening.

Although important physiological information can be obtained from brain waves, it is difficult to sufficiently evaluate a specific mental state with the brain waves only. Also, a system disclosed in Patent Document 1 can give the worker feedback of a satisfaction state, but the system is not a training system with which the worker who has become aware of the satisfaction state can change his/her own state by his/her own intention, grasp an effect of the change and control his/her own mental state.

Patent Document 2 discloses a system for determining a psychological state by grasping a correspondence between an operation speed (reaction speed) of a game, a psychological state, and physiological data of an adrenocorticotropic hormone (ACTH). In general, a stress is evaluated with ACTH. However, in Patent Document 2, it is not clear and not specific what psychological state is to be grasped. In addition, Patent Document 2 discloses a system for notifying a user of a determination result of a psychological state, but the system is not a training system with which a user, upon receiving the determination result, can control his/her own mental state himself/herself to change the psychological state and can then confirm a result of the change. Such a training system is considered to be technically difficult to achieve because ACTH is not an indicator that represents the result in real time. In addition, evaluating a specific mental state such as relaxation, awakening, sleepiness or tension with ACTH is difficult.

Patent Document 3 discloses a system that detects brain waves, evaluates comfort from the brain wave information and controls a device on a basis of a determination result. Patent Document 3 discloses that relaxation and awakening can be evaluated with brain waves only but accuracy of the evaluation is further increased by adding electrocardiographic data thereto. In addition, Patent Document 3 discloses a system that receives a comfort evaluation result and controls a device accordingly, but the system is not a training system with which a user changes his/her own mental state himself/herself and grasps an effect of the change.

Patent Document 4 discloses a device that records a movement of a line of vision of a driver with a CCD camera and outputs a warning when a distraction degree of the vehicle occupant is high. The distraction degree is determined from an image analysis result of the recording. The mental state is a specific content such as "distraction degree". The mental state, however, is not physiological data but one obtained from evaluation of recorded facial expression. In addition, a determination result is fed back to a machine but does not prompt a human to attempt to control his/her own mental state himself/herself upon receipt of the result.

Patent Document 5 discloses a system that measures physiological information of an infant and estimates his/her psychological state. The system thus can send a report via its emergency reporting unit in a case where the system judges that an abnormality has happened to the infant. A physiological value is obtained by measuring a pulse, and enables judgement such as that an infant is crying owing to sleepiness or whether an infant is in a dangerous state of lying prone. The system can notify a human of a judgement result but does not prompt the human to attempt to control himself/herself upon receipt of the result.

As disclosed in the above Patent Documents, the related arts have conventionally indicated a configuration of a system that measures physiological information, estimates a psychological state, displays an evaluation result and, possibly, further gives feedback to a machine. However, the system does not continuously chronologically present a mental state to a subject in real time. Therefore, a subject cannot perform training of controlling his/her own mental state himself/herself upon receipt of a presented mental state obtained from evaluation of a physiological measurement value.

In addition, the physiological measurement value is often evaluated by a single measurement value, which is only a brain wave, saliva (ACTH) or a pulse. The single measurement value can certainly estimate a psychological state to some degree. However, for a more accurate estimation of a specific mental state, a plurality of indicators are preferably used. The pulse represents an autonomic nerve activity, and the brain wave represents a central nerve activity. They enable evaluation of a specific mental state but cause difficulty in evaluation of a complex and specific mental state. In addition, the system is not intended for training and thus is terminated at a stage at which the result has been displayed. Therefore, the system is not a system with which a subject performs training upon receipt of the result and learns an effect of the training himself/herself. Also, many documents disclose a system that gives feedback to a machine, but such a system does not instruct a subject to subsequently take a specific action.

Patent Document 6 discloses a mental training system that grasps a mental state by using both brain wave information and electrocardiographic information, and performs mental training by giving feedback to a subject. Use of both the brain wave information and the electrocardiographic information enables accurate grasp of a mental state. However, brain wave information is a weak signal of approximately $\mu V$, whereas an electrocardiographic signal is an mV level. Even though the brain wave information signal can be obtained in a laboratory, it is extremely difficult to be measured outdoors, particularly in a noisy environment such as an intense exercise site or an actual working site.

In addition, even in electrocardiographic measurement, a subject has difficulty in playing an intense sport or performing actual work with an electrocardiograph being mounted on him/her, which is used in a medical examination. Furthermore, wearing such a measuring apparatus on his/her own body may be stressful itself. Therefore, even though mental information is grasped in a state that such an apparatus is being mounted, the grasped mental information deviates from its actual state. As a result, the mental training system is difficult to be used for appropriate training.

PRIOR ART DOCUMENTS

Patent Documents

Patent Document 1: JP-A-10-262942
Patent Document 2: JP-A-2004-267296
Patent Document 3: JP-A-8-71050
Patent Document 4: JP-A-8-290725
Patent Document 5: JP-A-2004-181218
Patent Document 6: Japanese Patent No. 4844523

SUMMARY OF THE INVENTION

Technical Problem

The present invention has been made considering these circumstances, and an object of the present invention is to provide a training system that grasps a mental state with a garment-type biometric information measuring apparatus and, through feedback, utilizes the grasped mental state in training. The garment-type biometric information measuring apparatus is easily worn and does not give a sense of discomfort to a wearer upon his/her wearing it.

Solutions to the Problems

As a result of intensive studies to achieve the above object, the present inventors have developed a garment-type biometric information measuring apparatus (sensing wear or wearable smart device) that is easily worn and does not give a sense of discomfort to a wearer upon his/her wearing it. The present inventors have thus invented a biometric information presentation system utilizing the garment-type biometric information measuring apparatus and invented a training method utilizing the system.

That is, the present invention has the following configuration.

[1] A biometric information presentation system that two-dimensionally shows biometric information by plotting an interbeat interval and an indicator of parasympathetic activity that are obtained from electrocardiographic information of a subject on respective coordinate axes of a Cartesian coordinate system to present a psychological and physiological state of the subject.

[2] A biometric information presentation system that two-dimensionally shows biometric information by plotting an interbeat interval and an indicator of sympathetic activity that are obtained from electrocardiographic information of a subject on respective coordinate axes of a Cartesian coordinate system to present a psychological and physiological state of the subject.

[3] The biometric information presentation system according to [1] or [2], that uses an RRI as the interbeat interval, wherein the RRI is an interval between R waves of an electrocardiographic signal.

[4] The biometric information presentation system according to [1] or [2], that calculates LF and HF, wherein the LF is a definite integral value of a power spectrum from frequencies $L_{f1}$ to $L_{f2}$, the power spectrum is obtained by a procedure including a step of converting the interbeat interval to a frequency spectrum, the HF is a definite integral value of the power spectrum from frequencies $H_{f1}$ to $H_{f2}$, the $H_{f1}$ is greater than the $L_{f1}$, the $H_{f2}$ is greater than the $L_{f2}$, the HF is used as the indicator of the parasympathetic activity, and (the LF/the HF) is used as the indicator of the sympathetic activity.

[5] The biometric information presentation system according to any of [1] to [4], wherein the electrocardiographic information is obtained by a garment-type biometric information measuring apparatus.

[6] The biometric information presentation system according to any of [1] to [5], wherein the garment-type biometric information measuring apparatus includes at least fabric having a 20% elongation stress of 20 N or less, a garment pressure of the garment-type biometric information measuring apparatus is 0.1 kPa or more and 1.5 kPa or less, and a skin contact-type electrode is provided at a portion of the garment-type biometric information measuring apparatus at which a garment pressure is 0.3 kPa or more.

[7] The biometric information presentation system according to [6], wherein the skin contact-type electrode is an electrode including conductive fabric.

[8] The biometric information presentation system according to [6], wherein the skin contact-type electrode is an electrode including a stretchable conductor composition.

[9] The biometric information presentation system according to [6], wherein the skin contact-type electrode is an electrode including a conductive gel.

[10] The biometric information presentation system according to any of [1] to [9], having a unit that conveys to the subject an action instruction prepared in advance on a case-by-case basis depending on the presented psychological and physiological state of the subject.

[11] A training method for performing training of work with the biometric information presentation system according to any of above [1] to [10].

[12] The training method according to [10] or [11], wherein the work is sport.

[13] The training method according to [10] or [11], wherein the work is an instrumental performance.

[14] The training method according to [10] or [11], wherein the work is a machine operation.

The present invention preferably further has the following configuration.

[15] The biometric information presentation system, wherein the garment-type biometric information measuring apparatus according to above [4] or [5] includes a wire formed from a stretchable conductive material.

[16] The biometric information presentation system, wherein the stretchable conductive material is a layer (a film, a sheet or a membrane) including the stretchable conductor composition.

[17] The biometric information presentation system, wherein the stretchable conductive material is conductive yarn stitched into fabric in a zigzag.

[18] The biometric information presentation system, wherein the stretchable conductive material is conductive yarn incorporated in knit fabric.

[19] The biometric information presentation system, wherein the stretchable conductive material is an electrical wire or a metal foil pattern that is arranged with redundancy, or the like.

[20] The biometric information presentation system according to any of [3] to [10] or [15] to [19], and the training method according to any of [11] to [14], wherein the biometric information is two-dimensionally shown by plotting the interbeat interval and the indicator of the parasympathetic activity that are obtained from the electrocardiographic information of the subject on the respective coordinate axes of the Cartesian coordinate system, the biometric information is two-dimensionally shown by plotting the interbeat interval and the indicator of the sympathetic activity that are obtained from the electrocardiographic information of the subject on the respective coordinate axes of the Cartesian coordinate system, and both the pieces of the two-dimensionally shown biometric information are simultaneously presented.

Advantageous Effects of the Invention

In the present invention, the interbeat interval can be a value reflecting stress that a body undergoes directly. On the other hand, the indicator of the parasympathetic activity represents a relaxation degree of automatic nerves, and the indicator of the sympathetic activity represents an activity degree of the automatic nerves. In the present invention, the interbeat interval is denoted by an abscissa, and the indicator of the parasympathetic activity or the indicator of the sympathetic activity is denoted by an ordinate, for example. On each of these abscissa and ordinate is plotted a corresponding usual state of the subject, and then plotted a state of the subject in training, a match, or the like. Plotting such states in this manner enables the subject himself/herself or his/her coach to intuitively grasp how his/her automatic nervous activity is activated under stress compared to the usual state.

Performing training with the system enables conscious control of the sympathetic activity and the parasympathetic activity. Repeating the training enables such rectification as to prevent the subject from becoming more nervous than is necessary or becoming too relaxed upon an actual match. In addition, further autonomous training is enabled by stocking the system in advance with the action instructions depending on the psychological and physiological state of the subject on a basis of his/her personal character, and by incorporating into the system such a mechanism as to automatically convey the instructions in response to the shown biometric information or manually convey them by an operation of the subject in response to it. The autonomous training enables effective utilization of the present system even in a case, such as in a match, where the subject is unable to receive an instruction from the coach.

The present invention can obtain necessary information for the training from just the electrocardiographic information without using brain wave information. The brain wave information is weak and susceptible to noise, compared to the electrocardiographic signal. This renders, particularly, in-situ detection of the brain wave information difficult. In addition, detection of the brain waves necessitates an electrode attached to a head, thus becoming difficult upon an action that might cause a strenuous movement, a collision, or the like. The present invention can obtain, from just the electrocardiographic information, a value reflecting stress that a body undergoes directly and, simultaneously, the activity degree of the automatic nerves, such as the indicator of the parasympathetic activity and the indicator of the sympathetic activity, that is susceptible to psychological and mental responses. The present invention then two-dimensionally shows the value and the activity degree, consequently enabling a grasp of the psychological and physiological state from just the electrocardiographic information.

In the present invention, the garment-type biometric information measuring apparatus is preferably used to obtain the electrocardiographic information. Such a garment-type biometric information measuring apparatus has the proper garment pressure, thus enabling to be worn by a wearer without giving a sense of discomfort to him/her. In addition, the garment-type biometric information measuring apparatus allows the skin contact-type electrode to be disposed on a portion having a proper contact pressure, ensuring signal detection and not giving the wearer a sense of peculiar discomfort at the electrode portion. As a result, with the biometric information measuring apparatus being worn, the wearer can naturally perform an action, such as the sport and the work, enabling in-situ detection of natural electrocardiographic information. Further, the biometric information measuring apparatus is in relatively close contact with a body so that the body itself functions as a buffer for noise whereby an SN ratio is improved.

BRIEF DESCRIPTION OF DRAWINGS

FIG. 1 is an example of a typical electrocardiographic waveform.

FIG. 2 is an explanatory figure of a concept of determining LF and HF from a frequency analysis of an electrocardiographic waveform.

FIG. 3 is a block diagram of a biometric information presentation system of the present invention.

FIG. 4 is an example in which an RRI is plotted on an abscissa and an indicator of parasympathetic activity is plotted on an ordinate.

FIG. 5 is an example in which an RRI is plotted on an abscissa and an indicator of sympathetic activity is plotted on an ordinate.

DESCRIPTION OF EMBODIMENTS

Described is a method for determining an interbeat interval, an indicator of parasympathetic activity and an indicator of sympathetic activity from electrocardiographic information in a biometric information measuring apparatus of the present invention.

The electrocardiographic information can be obtained as an electrical signal. For the electrical signals, voltage measurement may be chronologically performed through a biometric contact type electrode.

The interbeat interval denotes an interval between heartbeats or pulses (unit: ms). The heartbeat interval is obtained by reading an interval between R waves from an electrocardiogram or by measuring an interval between adjacent heartbeats. The pulse interval is obtained by measuring an interval between adjacent pulses. The interbeat interval or oscillation thereof ostensibly indicates a neuropsychiatric state. The interbeat interval or the oscillation thereof can ostensibly be an indicator of physical and mental stress and reflects a balance of the neuropsychiatric state of a sympathetic nerve and parasympathetic nerve, which belong to an automatic nervous system.

The interbeat interval is preferably an R-R interval (hereinafter referred to as an "RRI") between R waves in an electrocardiographic signal. The RRI clearly shows a peak of the signal and thus hardly causes misrecognition of a peak position, consequently enabling to improve accuracy of the interbeat interval.

The indicator of the sympathetic activity and the indicator of the parasympathetic activity of the present invention may be values obtained from frequency spectrum analysis of the interbeat interval. More specifically, the frequency spectrum analysis includes calculation of LF and HF. The LF is a definite integral value of a power spectrum from frequencies $L_{f1}$ to $L_{f2}$. The power spectrum is obtained by a procedure including a step of converting the interbeat interval to a frequency spectrum. The HF is a definite integral value of the power spectrum from frequencies $H_{f1}$ to $H_{f2}$. The $H_{f1}$ is greater than the $L_{f1}$, and the $H_{f2}$ is greater than the $L_{f2}$. The HF is used as the indicator of the parasympathetic activity, and (the LF/the HF) is used as the indicator of the sympathetic activity.

For example, the LF may be a definite integral value of a power spectrum F2 (a first power spectrum) from frequencies $L_{f1}$ to $L_{f2}$. The power spectrum F2 is obtained by converting the interbeat interval, which is a time signal f, to a frequency spectrum (a frequency spectrum F) and then by squaring the frequency spectrum. The HF may be a definite integral value of the power spectrum F2 (the first power spectrum) from frequencies $H_{f1}$ (>$L_{f1}$) to $H_{f2}$ (>$L_{f2}$).

A unit of the LF and the HF, which are calculated with the first power spectrum $F_2$ is $ms^2$. A frequency spectrum conversion method may be, for example, fast Fourier transform (FFT), wavelet analysis, a maximum entropy method, or the like. The present specification describes a case using FFT as an example, but another method can also be used certainly.

A detailed calculation method of the LF and HF is described with FIG. 2. FIG. 2 shows an explanatory figure of a power spectrum integral according to the present invention. In FIG. 2, an ordinate denotes power spectral density (unit: $ms^2/Hz$), and an abscissa denotes a frequency (unit: Hz). The LF is a definite integral value of a power spectrum (for example, the first power spectrum F2) from, for example, 0.04 Hz ($L_{f1}$) to 0.15 Hz ($L_{f2}$), and corresponds to an area of a portion hatched by oblique lines in FIG. 1. The $L_{f1}$ is less than the $L_{f2}$. On the other hand, the HF is a definite integral value of a power spectrum (for example, the first power spectrum F2) from, for example, from 0.15 Hz ($H_{f1}$) to 0.4 Hz ($H_{f2}$), and corresponds to an area of a portion hatched by vertical lines in FIG. 2. The $H_{f1}$ is less than $H_{f2}$. In FIG. 2, an integral range is set in a manner that the $L_{f2}$ and the $H_{f1}$ become equally 0.15 Hz, but the $L_{f2}$ and the $H_{f1}$ may be the same or different values as long as they satisfy a relation of $L_{f1}$<$H_{f1}$ and $L_{f2}$<$H_{f2}$. Here, the method of the power spectrum integral has been described with the first power spectrum F2, but a definite integral with the second power spectrum F can be similarly calculated.

The power spectrum obtained by the frequency spectrum conversion is classified into the LF, which is a component deriving from variation of blood pressure and is also referred to as a Mayer-Wave related component, and into the HF, which is a component deriving from respiration. The blood pressure variation component LF is the power spectrum of around 0.1 Hz and is related to both sympathetic activity and parasympathetic activity. On the other hand, the respiration-derived component HF is the power spectrum of around 0.3 Hz and is considered to be related to parasympathetic activity. From the foregoing, an integral range of the LF indicating sympathetic activity and parasympathetic activity at least includes 0.1 Hz and is preferably $L_{f1}$<0.1<$L_{f2}$. The $L_{f1}$ is more preferably 0.03 Hz or more, and further preferably 0.04 Hz or more. Also, the $L_{f1}$ is preferably 0.05 Hz or less, and more preferably 0.045 Hz or less. The $L_{f2}$ is preferably 0.13 Hz or more, and more preferably 0.14 Hz or more, and also is more preferably 0.16 Hz or less, and further preferably 0.15 Hz or less. An integral range of the HF indicating parasympathetic activity at least includes 0.3 Hz and is preferably $H_{f1}$<0.3<$H_{f2}$. The $H_{f1}$ is more preferably 0.14 Hz or more, further preferably 0.15 Hz or more, and may be 0.17 Hz or less, or 0.16 Hz or less. The $H_{f2}$ is preferably 0.38 Hz or more, and more preferably 0.39 Hz or more, and more preferably 0.41 Hz or less, and further preferably 0.4 Hz or less.

As a result of examinations by the inventors, the following phenomenon has been observed. Upon work with concentration, the RRI and the parasympathetic activity become small, or the RRI and the sympathetic activity become small. From this observation, the inventors have found that two-dimensionally showing the RRI and the indicator of the parasympathetic activity, or the RRI and the indicator of the sympathetic activity can present a psychological and physiological state of a subject.

For example, a worker grasps his/her RRI and an indicator of his/her parasympathetic activity, or his/her RRI and an indicator of his/her sympathetic activity in his/her psychological and physiological state that he/she considers best. With this grasp, the worker can train himself/herself to approximate his/her RRI and an indicator of his/her parasympathetic activity, or his/her RRI and an indicator of his/her sympathetic activity to such a best level upon image training or mental training.

In the present invention, the electrocardiographic information can be obtained through the biometric contact type electrode from the voltage measurement performed chronologically. An input impedance of a voltage measuring unit is 100 kΩ or more, preferably 300 kΩ or more, further preferably 1 MΩ or more. An upper limit of the input impedance is not limited.

A garment which becomes a base of the garment-type biometric information measuring apparatus of the present invention is made of fabric having a 20% elongation stress of 20 N or less. A garment pressure thereof is set to be 0.1 kPa or more and 1.5 kPa or less. The garment pressure is premised on a person who has a standard shape, but a shape of a subject and a size of a garment may be adjusted in manner that a garment pressure falls within the allowable range.

In the present invention, a skin contact-type electrode is disposed at a portion at which the garment pressure is 0.3 kPa or more. In general, the skin contact-type electrode is often brought into contact with a body with needlessly high pressure to achieve reliable contact. However, such a disposition is unable to remove a sense of discomfort from the subject, thus being unable to obtain effective biometric information.

The present invention can use, instead of the electrocardiographic information, pulse wave information that captures a change in a blood flow rate rather than a biometric potential. The pulse wave can be measured at a wrist or a finger. In addition, a difference between the electrocardiographic information and the pulse wave information at a position distant from a heart enables calculation of a parameter relating to blood pressure.

Next, a signal processing unit that processes a signal from a detection unit will be described. From the electrocardiographic information, the R wave is detected, and a time interval between the R waves (RRI) is determined. The R wave has the largest amplitude amongst waves of the electrocardiographic information. A typical electrocardiographic waveform is shown in FIG. 1.

The present invention achieves a biometric information measuring environment that does not give a subject a sense of discomfort, thus being able to evaluate a mental state of the subject from just the electrocardiographic information without using brain wave information.

Next will be described an evaluation result presentation unit that continuously chronologically presents a mental evaluation result to a subject in real time. The evaluation result presentation unit shows on a monitor screen a signal processing result indicating an RRI and an indicator of parasympathetic activity, and/or an indicator of sympathetic activity that are obtained from an electrocardiographic signal.

Preferably, the RRI of the electrocardiographic information is plotted on an X axis, and the indicator of the parasympathetic activity and the indicator of the sympathetic activity are plotted on a Y axis in order that a chronological change can be seen. In the above manner, a value per unit time (for example, every second) is continuously plotted. To easily see lapse of time, preference is given to a method of, for example, changing a color density chronologically or changing a color every minute. Upon long-time training, the result can be presented with a much longer presentation interval than 1 second.

The plotting is initiated at a center after a start of training. This can elucidate a change to be presented. Ranges of the X axis and Y axis may also be changed and presented as the plotting increases so that the ranges can be presented in a full screen. In such a manner, psychological and physiological biometric information can be visually presented. In the present invention, the real time means that a mental information evaluation result is presented whenever it is obtained. In a case where evaluation calculation requires time, a delay corresponding to the time is allowed until the result is presented.

Next, an action presentation unit that presents a specific recommended action will be described. Upon an operation performed by a subject himself/herself, the subject selects "relaxation" of a desired mental selection screen on a monitor when the subject feels inclined to relax more upon confirming his/her mental state evaluation result. In response to this, an instruction such as "Close your eyes and take a deep breath" is presented on the monitor. When the subject makes a selection to be in a more tense state, an instruction such as "Deliberately take a quick breath" is presented on the monitor.

In a case where the subject feels inclined to become more awakened upon confirming his/her mental state evaluation result, the subject selects "awakening" of the desired mental selection screen on the monitor. In response to this, an instruction such as "Close your eyes and think a pleasant plan such as your hobby" is presented on the monitor. In a case where the subject makes a selection to become sleepier, an instruction such as "Close your eyes and do not think about anything" is presented on the monitor. Specific contents of the instructions are not limited to the contents described above and also includes an instruction of performing calisthenics or eating food. In addition, in a case where the subject feels inclined to maintain his/her mental state, the subject selects "No change" that represents the subject's inclination to maintain his/her mental state. These instructions may be presented chronologically, or presented automatically upon a significant change in the subject's psychological and physiological state, which is detected automatically by a device. Such a presentation method is an embodiment of the present invention, and the present invention is not limited thereto.

Hereinabove is described the case where the subject himself/herself performs the operation upon confirming a presentation result. However, a supervisor or a trainer of the subject can perform an appropriate action presentation upon confirming the presentation result. Utilization of the present system enables performance of an appropriate action presentation based upon physiological data, thus enabling performance of training with higher quality.

In the present invention, the skin contact-type electrode may be an electrode including conductive fabric. The conductive fabric is woven fabric, non-woven fabric, knit fabric, embroidery yarn, sewing yarn, or the like that is formed of fiber including at least conductive yarn.

The conductive yarn preferably has a resistance value of 100Ω or less per 1 cm of its fiber length. The conductive yarn is a general term for conductive fiber, a fiber bundle of conductive fiber, twisted yarn, plaited yarn, spun yarn, and blended yarn obtained from fiber including conductive fiber, a fine metal wire obtained by finely stretching a metal wire, and a fine film obtained by cutting a film into a fine fiber shape.

Examples of the conductive fiber include chemical fiber or natural fiber coated with a metal, chemical fiber or natural fiber coated with a conductive metal oxide, chemical fiber or natural fiber coated with a carbon-based conductive material, such as graphite, carbon, carbon nanotube, and graphene, and chemical fiber or natural fiber coated with a conductive polymer.

In addition, the conductive fiber is, for example, obtained by spinning a polymer material including at least one conductive material selected from the group consisting of a metal, a conductive metal oxide, a carbon-based conductive material and a conductive polymer.

The fiber bundle of conductive fiber is, for example, obtained by making a fiber bundle formed of micro fiber or nanofiber of the conductive fiber carry and impregnated with a conductive filler, a conductive polymer, or the like.

The conductive yarn may be the twisted yarn, the plaited yarn, the spun yarn, or the blended yarn obtained from fiber including the conductive fiber. The conductive yarn also includes the fine metal wire obtained by finely stretching a metal wire.

An average diameter of each of the conductive fiber, the fiber bundle of conductive fiber, the twisted yarn, the plaited yarn, the spun yarn, and the blended yarn that are obtained from fiber including the conductive fiber, and the fine metal wire is preferably 250 μm or less, more preferably 120 μm or less, further preferably 80 μm or less, and particularly preferably 50 μm or less.

The conductive yarn also includes the fine film obtained by cutting a film into a fine fiber shape. The fine film refers to a fibrous film obtained by cutting to a width of 800 μm or less a polymer film coated with at least one conductive material selected from the group consisting of a metal, a conductive metal oxide, a carbon-based conductive material and a conductive polymer.

Amongst the conductive yarns, a preference is given to at least one selected from the group consisting of chemical fiber coated with a metal, a fiber bundle of conductive fiber that is made to carry and be impregnated with a conductive polymer, and a fine metal wire having an average diameter of 50 μm or less.

Specific examples of the conductive fabric include fiber structure obtained by embroidering the conductive yarn on non-conductive cloth, fiber structure obtained by impregnating non-conductive cloth with a conductive polymer-containing solution and performing drying, and fiber structure obtained by performing impregnation with a solution containing a conductive filler and a binder resin and performing drying. Amongst these, preference is given to the fiber structure obtained by impregnating non-conductive cloth with a conductive polymer-containing solution and performing drying.

The conductive polymer may be preferably a mixture containing poly(3,4-ethylenedioxythiophene) and polystyrene sulfonic acid, for example.

The fiber including the conductive yarn is preferably a synthetic fiber multifilament. At least a part of the synthetic fiber multifilament is preferably a fine filament having a fineness of less than 30 dtex or is preferably a synthetic fiber multifilament having a fineness of more than 400 dtex and a single fiber fineness of 0.2 dtex or less.

In a case where the conductive fabric is textile or knit formed of fiber including the conductive yarn, a basis weight is preferably less than 50 g/m$^2$, whereby the conductive polymer can be prevented from falling off. In addition, the basis weight is preferably more than 300 g/m$^2$, whereby a sufficient conductivity can be achieved.

The skin contact electrode of the present invention may be an electrode including a stretchable conductor composition. The stretchable conductor layer refers to a layer having stretchability and a specific resistance of $1 \times 10^0$ Ωcm or less. The stretchability means that 10% or more stretch can be repeated while conductivity is maintained. The stretchable conductor layer alone preferably has a breaking elongation of 40% or more. The breaking elongation is more preferably 50% or more and further preferably 80% or more.

The breaking elongation can be measured in the following manner. A conductive paste is coated on a release sheet at a predetermined thickness and dried, and then the release sheet is peeled off. Thereafter, a tensile test is performed for the measurement.

The stretchable conductor layer preferably has a tensile modulus of 10 to 500 MPa.

The stretchable conductor layer has an average thickness of preferably 20 μm or more and 50 μm or less, for example. The average thickness is more preferably 500 μm or less, further preferably 250 μm or less, and particularly preferably 90 μm or less.

A material that can form such a stretchable conductor layer may be hereinafter referred to as a stretchable conductor layer composition. The stretchable conductor layer can be formed from, for example, a conductive paste as the stretchable conductor layer composition.

The conductive paste contains at least (i) a conductive particle, (ii) a flexible resin, and (iii) a solvent.

(i) Conductive Particle

The conductive particle refers to a particle having a specific resistance of $1 \times 10^{-1}$ Ωcm or less.

Examples of the particle having a specific resistance of $1 \times 10^{-1}$ Ωcm or less include a metal particle, an alloy particle, a carbon particle, a carbon nanotube particle, a doped semiconductor particle, a conductive polymer particle and a hybrid particle.

Examples of the metal particle include a silver particle, a gold particle, a platinum particle, a palladium particle, a copper particle, a nickel particle, an aluminum particle, a zinc particle, a lead particle and a tin particle.

Examples of the alloy particle include a brass particle, a bronze particle, a cupronickel particle and a solder particle. Examples of the doped semiconductor particle include an oxide of tin and a composite oxide of indium and tin. Examples of the conductive polymer particle include a particle including a mixture containing poly(3,4-ethylenedioxythiophene) and polystyrene sulfonic acid, and a polymer particle coated with a metal. Examples of the hybrid particle include a metal particle coated with a metal, a glass particle coated with a metal and a ceramic particle coated with a metal. An example of the metal particle coated with a metal includes a silver-coated copper particle.

The conductive particles have an average particle diameter of, for example, preferably 100 μm or less, more preferably 30 μm or less, and further preferably 12 μm or less. A lower limit of the average particle diameter is, for example, 0.08 μm or more but not particularly limited thereto.

The particle may be, for example, flake-shaped powder or amorphous agglomerated powder. The silver particle may be, for example, a flake-shaped silver powder or amorphous agglomerated silver powder.

The flake-shaped powder has an average particle diameter (50% D), which is measured by a dynamic light scattering method, of preferably 0.5 to 20 μm, for example. Flake-shaped powder having an average particle diameter of less than 0.5 μm might cause deterioration of conductivity because its particles may not come into contact with one another. The average particle diameter is more preferably 3 μm or more and further preferably 5 μm or more. However, an average particle diameter exceeding 20 μm may cause difficulty in forming a fine wire. Such an average diameter may also cause clogging when screen printing or the like is performed. The average particle diameter is more preferably 15 μm or less and further preferably 12 μm or less.

The amorphous agglomerated powder has an average particle diameter (50% D), which is measured by a light confusion method, of preferably 1 to 20 μm, for example. Amorphous agglomerated powder having an average particle diameter of less than 1 μm may lose an effect as agglomerated powder, thus being unable to maintain conductivity in some cases. The average particle diameter is more preferably 3 μm or more and further preferably 5 μm or more. However, an average particle diameter exceeding 20 μm lowers dispersibility in a solvent, thus causing difficulty in forming a paste. The average particle diameter is more preferably 15 μm or less and further preferably 12 μm or less.

(ii) Flexible Resin

The flexible resin may be a thermoplastic resin, a thermosetting resin or rubber that has an elastic modulus of 1 to 1000 MPa. Preference is given to the rubber in order for a film to exhibit stretchability. The elastic modulus is preferably 3 MPa or more, more preferably 10 MPa or more and further preferably 30 MPa or more. The elastic modulus is preferably 600 MPa or less, more preferably 500 MPa or less and further preferably 300 MPa or less.

Examples of the thermoplastic resin may include polyethylene, polyvinyl chloride, polystyrene, polyvinyl acetate, polyurethane, an acrylic resin, polyamide and polyester. Examples of the thermosetting resin may include a phenolic resin, an epoxy resin, a melamine resin and a silicone resin.

Examples of the rubber include urethane rubber, acrylic rubber, silicone rubber, butadiene rubber, nitrile group-containing rubber, such as nitrile rubber and hydrogenated nitrile rubber, isoprene rubber, sulfide rubber, styrene butadiene rubber, butyl rubber, chloroprene rubber, chlorosulfonated polyethylene rubber, ethylene propylene rubber and a vinylidene fluoride copolymer. Amongst these, preference is given to the nitrile group-containing rubber, the chloroprene rubber and the chlorosulfonated polyethylene rubber, and particular preference is given to the nitrile group-containing rubber.

The nitrile group-containing rubber is any rubber or any elastomer containing a nitrile group and not particularly limited thereto. The nitrile group-containing rubber is preferably the nitrile rubber or the hydrogenated nitrile rubber, for example. The nitrile rubber is a copolymer of butadiene and acrylonitrile. A large amount of bonding acrylonitrile increases affinity with a metal but decreases rubber elasticity contributing to stretchability. Therefore, the amount of the bonding acrylonitrile in the acrylonitrile-butadiene copolymer rubber is preferably 18 to 50% by mass and more preferably 40 to 50% by mass.

A content of the flexible resin is 7 to 35% by mass relative to a total amount of the conductive particle and the flexible resin. The content is more preferably 9% by mass or more, and further preferably 12% by mass or more, and more preferably 28% by mass or less, and further preferably 20% by mass or less.

(iii) Solvent

The solvent may be a well-known organic solvent or aqueous solvent and is not particularly limited thereto.

A surface of the electrode, which is a side in contact with skin of a wearer, preferably has an electrode surface layer. On the other hand, at a boundary between the electrode and the cloth portion is preferably provided a base layer for enhancement of an insulating property.

(Electrode Surface Layer)

Examples of the electrode surface layer include a noble metal plating layer, a metal layer that is hardly oxidized owing to a formation of a passive state, a corrosion-resistant alloy layer, a carbon layer, and a stretchable conductive layer. These layers may be provided alone or provided by being laminated into two or more layers.

An example of the noble metal plating layer includes at least one layer selected from the group consisting of gold, silver, platinum, rhodium and ruthenium.

An example of the metal layer that is hardly oxidized owing to a formation of a passive state includes one layer selected from the group consisting of chromium, molybdenum, tungsten and nickel.

An example of the corrosion-resistant alloy layer includes a Monel alloy layer.

The carbon layer is preferably formed by printing, for example, a carbon paste on the surface of the electrode.

The stretchable conductive layer is preferably formed from the stretchable conductive composition containing, for example, a conductive filler and the flexible resin.

The skin contact-type electrode of the present invention may be a conductive gel. The conductive gel may be construed as a gel electrode material used for a surface of a skin contact-type electrode of a medical instrument.

EXAMPLES

[Preparation of Conductive Paste]

A conductive paste for forming a stretchable conductor was prepared in the following manner with the following blend: 10 parts by mass of a binder, 70 parts by mass of a silver particle, 1 part by mass of a carbon particle and 19 parts by mass of a solvent. The binder resin was firstly dissolved in the solvent of half the predetermined amount. To the resultant solution were added the metal particle and the carbon particle. After being premixed, this solution was dispersed by a three-roll mill, and the paste was thereby prepared. The binder was Coatron KYU-1 (glass transition temperature: −35° C.) manufactured by SANYO CHEMICAL, LTD. The silver particle was micro-diameter silver powder SPH02J (average particle diameter: 1.2 μm) manufactured by MITSUI MINING & SMELTING CO., LTD. The carbon particle was Ketjen black EC600JD manufactured by LION SPECIALTY CHEMICALS CO., LTD. The solvent was butyl carbitol acetate.

The paste, which had been thus prepared, for forming a stretchable conductor was screen printed at a thickness of 25 μm. The screen-printed paste was then dried at 100° C. for 20 minutes to obtain a layer of the stretchable conductor (stretchable conductor sheet). The stretchable conductor layer had an initial specific resistance of 250 μΩ·cm and had such stretchability as to maintain its conductivity even after 20% elongation repeated 100 times.

[Preparation of Stretchable Carbon Paste]

A carbon paste for an electrode protective layer was prepared according to the composition shown in Table 2. The carbon paste having stretchability was prepared by premixing the following materials and then dispersing the premixture: 40 parts by mass of a nitrile butadiene rubber resin having a glass transition temperature of −19° C., 20 parts by mass of Ketjen black EC300J manufactured by LION SPECIALTY CHEMICALS CO., LTD., and 50 parts by mass of ethylene glycol monoethyl ether acetate, which was used as a solvent.

With the stretchable carbon paste and the stretchable conductor paste, an electrode and a wire were formed on a release sheet in the following manner. To this release sheet, which was made of PET, whose surface had been treated with a silicone-based release agent was provisionally adhered a urethane sheet (corresponding to an insulating cover layer). This urethane sheet had a predetermined shape of having cut-out portions for an electrode and a connector. After the provisional adhesion, at this cut-out portion for an electrode was screen printed the stretchable carbon paste, and then from this cut-out electrode portion to the cut-out portion for a connector was printed the stretchable conductor paste in a predetermined pattern. On the urethane sheet was then laminated a double-sided hot melt sheet (corresponding to an insulating base layer) as it covered the urethane sheet, and thereby the electrode and the wire were formed.

The electrode and the wire, which have been thus obtained, on the release sheet can be transferred to an electrode support portion together with the insulating base layer and the insulating cover layer. This transfer is performed in the following manner. The electrode and the wire are laid on fabric for a garment, as their side, which is a side of the double-sided hot melt sheet, comes into contact with the fabric, and then they are heated and pressed with a hot press.

Example 1

A garment-type biometric information measuring apparatus that could simultaneously measure electrocardiographic information, myoelectric distribution information and respiration information was produced in the following manner. To a chest portion of a sport shirt made of fabric having a 20% elongation stress of 7 N were attached an electrocardiographic information measurement electrode, which included a stretchable conductor composition having a 20% elongation stress of 0.5 N. Around left and right arms were attached myoelectric distribution measurement electrodes including the same material as that of the electrocardiographic information measurement electrode (8 electrodes were disposed around each arm respectively). Around a chest was disposed a stretchable capacitor having a 20% elongation stress of 1.2 N. Then, attached was an electronic unit for detecting an electrode potential and a capacity change of the stretchable capacitor and for transmitting detected data to a portable terminal, and thereby the garment-type biometric information measuring apparatus was produced. When a subject wore the produced biometric information measuring apparatus, its maximum garment pressure was 0.6 kPa, a garment pressure of its electrocardiographic information measurement electrode-disposed portion was 0.4 kPa, and a garment pressure of its myoelectric measurement electrode-disposed portion was 0.6 kPa. The electrode including the stretchable conductor composition was prepared, with a hot press, by transferring the electrode and the wire that had been formed on the release sheet in advance. The electronic unit was equipped with a thermometer, GPS location information, an acceleration sensor for XYZ axes, and could also transmit these kinds of information to the portable terminal.

From electrocardiographic information obtained by the garment-type biometric information measuring apparatus were determined an RRI, an indicator of parasympathetic activity and an indicator of sympathetic activity, and a biometric information presentation system was obtained by delineating the following two charts and showing them on a tablet terminal: one chart used the RRI and the indicator of the parasympathetic activity for its X and Y axes respectively and the other chart used the RRI and the indicator of sympathetic activity for its X and Y axes.

A subject wore the garment-type biometric information measuring apparatus, and his/her trainer observed the tablet. The subject was a motor racing driver. Basic parameters of the subject, which were electrocardiogram (heartbeat), respiration, electromyogram and body surface temperature, were detected, while the subject was not driving a vehicle (in waiting), was performing image training, and was driving a vehicle (on race). From detected electrocardiographic information were calculated an RRI, an indicator of sympathetic activity and an indicator of parasympathetic activity. While the trainer was observing these kinds of information and giving an instruction accordingly, the subject performed training and competed in a race.

As a result, the trainer could give such an instruction as to induce the subject to be in a state that the subject felt concentrated yet did not feel too tense, on a basis of a mental state and a physiological state (fatigue state or the like) of the subject.

Example 2

A garment-type biometric information measuring apparatus that could simultaneously measure electrocardiographic information and respiration information was produced in the following manner. At an under-bust portion of a sport brassiere made of fabric having a 20% elongation stress of 5 N were disposed an electrocardiographic information measurement electrode including conductive fabric, and were disposed a stretchable capacitor having a 20% elongation stress of 1.2 N. Then, attached was an electronic unit for detecting an electrode potential and a capacity change of the stretchable capacitor and for transmitting detected data to a portable terminal, and thereby the garment-type biometric information measuring apparatus was produced. When a subject wore the produced biometric information measuring apparatus, its maximum garment pressure was 0.85 kPa, and a garment pressure of its electrocardiographic information measurement electrode-disposed portion was 0.8 kPa.

In the same manner as in Example 1, from obtained electrocardiographic information were determined an RRI, an indicator of parasympathetic activity and an indicator of sympathetic activity, and a biometric information presentation system was obtained by delineating the following two charts and showing them on a tablet terminal: one chart used the RRI and the indicator of the parasympathetic activity for its X and Y axes respectively and the other chart used the RRI and the indicator of the sympathetic activity for its X and Y axes.

A subject wore the garment-type biometric information measuring apparatus and performed training in a manner that his/her trainer observed the tablet. The subject was a vocalist. Various parameters of the subject were detected, in the same manner as in Example 1, during training, a rehearsal, dress rehearsal and a recital (actual performance). Detected parameters were utilized for image training assuming actual on-stage performance. As a result, the subject became capable of graceful artistic expression without feeling too tense during a recital.

INDUSTRIAL APPLICABILITY

As described above, the biometric information presentation system of the present invention can obtain biometric information during training in a natural state without giving a sense of discomfort to a wearer, and utilization of the system enables performance of efficient training.

The present invention can be broadly applied regardless of men and women and can be widely utilized in various kinds of sport training, such as ball game, gymnastics, swimming, shoot, Kyudo (Japanese art of archery), archery, throwing game and martial arts, driving training, such as a vehicle, a ship, an airplane and a heavy machine for civil engineering, skill training, such as wood working, iron working, metal carving, sewing working, dental technique, medical operation and cooking, performance training such as wind instrument, string instrument, percussion instrument and vocal musical, or art training, such as calligraphy, sculpture, embroidery and painting.

DESCRIPTION OF REFERENCE SIGNS

0 Subject
1 Biometric information detection unit
2 Signal processing unit
3 Evaluation unit
4 Evaluation result presentation unit
5 Action presentation unit

The invention claimed is:
1. A biometric information presentation system comprising:
   an evaluation result presentation unit that two-dimensionally shows biometric information by plotting an interbeat interval and an indicator of parasympathetic activity that are obtained from electrocardiographic information of a subject on respective coordinate axes of a Cartesian coordinate system to present a psychological and physiological state of the subject; and
   a unit that conveys to the subject an action instruction prepared in advance on a case-by-case basis depending on the presented psychological and physiological state of the subject.
2. The biometric information presentation system according to claim 1, wherein the system is configured to use an RRI as the interbeat interval, and the RRI is an interval between R waves of an electrocardiographic signal.

3. The biometric information presentation system according to claim 1, wherein the system is configured to calculate LF and HF, the LF is a definite integral value of a power spectrum from frequencies $L_{f1}$ to $L_{f2}$, the power spectrum is obtained by a procedure including a step of converting the interbeat interval to a frequency spectrum, the HF is a definite integral value of the power spectrum from frequencies $H_{f1}$ to $H_{f2}$, the $H_{f1}$ is greater than the $L_{f1}$, the $H_{f2}$ is greater than the $L_{f2}$, and the HF is used as the indicator of the parasympathetic activity.

4. The biometric information presentation system according to claim 1, wherein the electrocardiographic information is obtained by a garment-type biometric information measuring apparatus.

5. The biometric information presentation system according to claim 4, wherein the garment-type biometric information measuring apparatus includes at least fabric having a 20% elongation stress of 20 N or less, a garment pressure of the garment-type biometric information measuring apparatus is 0.1 kPa or more and 1.5 kPa or less, and a skin contact-type electrode is provided at a portion of the garment-type biometric information measuring apparatus at which a garment pressure is 0.3 kPa or more.

6. The biometric information presentation system according to claim 5, wherein the skin contact-type electrode is an electrode including conductive fabric.

7. The biometric information presentation system according to claim 5, wherein the skin contact-type electrode is an electrode including a stretchable conductor composition.

8. The biometric information presentation system according to claim 5, wherein the skin contact-type electrode is an electrode including a conductive gel.

9. A biometric information presentation system comprising:

an evaluation result presentation unit that two-dimensionally shows biometric information by plotting an interbeat interval and an indicator of sympathetic activity that are obtained from electrocardiographic information of a subject on respective coordinate axes of a Cartesian coordinate system to present a psychological and physiological state of the subject; and a unit that conveys to the subject an action instruction prepared in advance on a case-by-case basis depending on the presented psychological and physiological state of the subject.

10. The biometric information presentation system according to claim 9, wherein the system is configured to calculate LF and HF, the LF is a definite integral value of a power spectrum from frequencies $L_{f1}$ to $L_{f2}$, the power spectrum is obtained by a procedure including a step of converting the interbeat interval to a frequency spectrum, the HF is a definite integral value of the power spectrum from frequencies $H_{f1}$ to $H_{f2}$, the $H_{f1}$ is greater than the $L_{f1}$, the $H_{f2}$ is greater than the $L_{f2}$, and (LF/HF) is used as the indicator of the sympathetic activity.

11. The biometric information presentation system according to claim 9, wherein the electrocardiographic information is obtained by a garment-type biometric information measuring apparatus.

12. The biometric information presentation system according to claim 11, wherein the garment-type biometric information measuring apparatus includes at least fabric having a 20% elongation stress of 20 N or less, a garment pressure of the garment-type biometric information measuring apparatus is 0.1 kPa or more and 1.5 kPa or less, and a skin contact-type electrode is provided at a portion of the garment-type biometric information measuring apparatus at which a garment pressure is 0.3 kPa or more.

13. The biometric information presentation system according to claim 12, wherein the skin contact-type electrode is an electrode including conductive fabric.

14. The biometric information presentation system according to claim 12, wherein the skin contact-type electrode is an electrode including a stretchable conductor composition.

15. The biometric information presentation system according to claim 12, wherein the skin contact-type electrode is an electrode including a conductive gel.

* * * * *